(12) United States Patent
Middelbeek et al.

(10) Patent No.: US 8,961,485 B2
(45) Date of Patent: Feb. 24, 2015

(54) METHOD AND EQUIPMENT FOR FASTENING A THREAD TO A TAMPON

(75) Inventors: Hans Almer Middelbeek, Boxmeer (NL); Jozefus A. C. Smit, Boxmeer (NL)

(73) Assignee: Intervet International B.V., Boxmeer (NL)

( * ) Notice: Subject to any disclaimer, the term of this patent is extended or adjusted under 35 U.S.C. 154(b) by 635 days.

(21) Appl. No.: 13/319,711

(22) PCT Filed: May 11, 2010

(86) PCT No.: PCT/EP2010/056475
§ 371 (c)(1),
(2), (4) Date: Dec. 13, 2011

(87) PCT Pub. No.: WO2010/130746
PCT Pub. Date: Nov. 18, 2010

(65) Prior Publication Data
US 2012/0109095 A1    May 3, 2012

Related U.S. Application Data

(60) Provisional application No. 61/177,433, filed on May 12, 2009.

(30) Foreign Application Priority Data

May 12, 2009    (EP) ..................................... 09160023

(51) Int. Cl.
*A61F 13/20*    (2006.01)
(52) U.S. Cl.
USPC ................... 604/385.17; 604/385.18; 28/119; 28/120

(58) Field of Classification Search
USPC .................... 604/385.17, 385.18; 28/119, 120
See application file for complete search history.

(56) References Cited

U.S. PATENT DOCUMENTS

| | | | |
|---|---|---|---|
| 3,625,787 A | 12/1971 | Radl et al. | |
| 3,970,022 A | 7/1976 | Kopatz et al. | |
| 4,775,377 A | 10/1988 | Sweere | |
| 5,566,435 A * | 10/1996 | Brown, Jr. ....................... | 28/120 |
| 2003/0131456 A1 | 7/2003 | Rajala et al. | |

FOREIGN PATENT DOCUMENTS

GB    781890    8/1957

OTHER PUBLICATIONS

International Search Report corresponding to PCT/EP2010/056475, mailed Aug. 17, 2010.
European Search Report for European Application No. 09160023.9, dated Aug. 20, 2009.

* cited by examiner

*Primary Examiner* — Jacqueline F. Stephens

(57) ABSTRACT

A method for fastening a thread (24) to a tampon (10), in particular a veterinary tampon, comprising the steps of passing the thread through the tampon by means of a needle (12, 14), and knotting the loose ends of the thread, wherein that the step of passing the thread through the tampon comprises: -piercing the tampon (10) with two hollow needles (12, 14), -inserting the distal ends of the needles into a mould (20) that forms a passage (16) interconnecting the open ends of the hollow needles, feeding the thread (24) to the proximal end of one (12) of the two needles, -applying a suction pressure to the proximal end of the other (14) of the two needles, -opening the mould (20), and -withdrawing the needles (12, 14) from the tampon (10).

15 Claims, 8 Drawing Sheets

METHOD AND EQUIPMENT FOR FASTENING A THREAD TO A TAMPON

CROSS-REFERENCE TO RELATED APPLICATIONS

This application is a national stage entry under 35 U.S.C. §371 of PCT/EP20101056475 filed on May 11, 2010, which claims priority to U.S. Provisional Application No. 61/177, 433 filed on May 12, 2009, and EP Application No. 09160023.9 filed on May 12, 2009. The content of PCT/EP2010/056475 is hereby incorporated by reference in its entirety.

The invention relates to a method for fastening a thread to a tampon (i.e. a pack, pad, or plug made of cotton, sponge or other material, used i.a. to be inserted into a body cavity such as the nose, vagina, etc.) in particular a veterinary tampon, comprising the steps of passing the thread through the tampon by means of a needle, and knotting the loose ends of the thread.

Tampons, e. g. in the form of a cylindrical piece of sponge, are used for various purposes, for example for administering drugs or hormones to female mammals (including humans). The drug or hormone is applied, e.g. printed in parallel tracks, onto the circumferential surface of the cylindrical sponge which is then inserted into the vagina of the mammal. Such a treatment may be used for example for controlling the fertility cycle of sheep, cattle, swine etc.

In order to be able to withdraw the tampon from the vagina after a suitable treatment time, a thread has to be fastened to the tampon. In some cases, it requires considerable force to withdraw the tampon from the vagina, and consequently the fastening structure should be such that it can withstand a considerable tensile force without the sponge material being torn-up.

In the known method that has been described in the opening paragraph, thread is manually fastened to the tampon. This requires a considerable amount of time and labour and has also the drawback that it is difficult to assure controlled manufacturing circumstances.

It is therefore an object of the present invention to provide a method of the type indicated above which can at least partly be automated.

To that end, in the method according to the invention, the step of passing the thread through the tampon comprises:
piercing the tampon with two hollow needles,
inserting the distal ends of the needles into a mould that forms a passage interconnecting the open ends of the hollow needles,
feeding the thread to the proximal end of one of the two needles,
applying a suction pressure to the proximal end of the other of the two needles,
opening the mould, and
withdrawing the needles from the tampon.

In this way, the thread is caused to pass through the tampon twice, with an intermediate segment of the thread extending along a portion of the surface of the tampon on the side opposite where the loose ends of the thread exit the tampon. This fastening structure assures a high tensile strength. Further, these steps of the fastening process may easily be automated because they require only a simple manipulator for effecting the linear to-and-from movements of the two needles, in particular when the needles are arranged in parallel, a simple mechanism for opening and closing the mould, a simple thread dispensing mechanism that is capable of bringing one end of the thread close to the proximal end of one needle, and a suction device for applying a suction pressure to the proximal end of the other needle (i.e. imposing a pressure difference such that the pressure at the proximal end of the said other needle is lower than the pressure at the proximal end of the first needle; preferably, but not necessarily, this method comprises actual sucking at the proximal end of the said other of the two needles), with the result that the thread will automatically be forced through the needles and the passage in the mould.

Useful optional features of this method are indicated in the dependent claims.

In a preferred embodiment, the two needles are pierced through the tampon once again at other locations and in other directions, so that the thread is caused to pass through the tampon four times, with a segment of the thread passing through the tampon being separated by segments that extend along the surface thereof. In this second piercing step, the thread will be drawn through the tampon outside of the needles, and will make a sharp turn at the tip ends of the needles and proceed further into the hollow interior of the needles which will accommodate the loose ends of the thread. Then, a suction nozzle may be brought into the vicinity of the tip ends of the needles, so that the loose ends of the thread are drawn out of the needles and into the suction nozzle, so that the needles can be withdrawn while the loose ends of the thread are held in the suction nozzle before they are secured by a knot. Indeed, use can be made of another pressure difference generating device to apply a suction force at the distal ends of the needles, for example by generating a positive pressure at the proximal ends of the needles. This also results in a net suction force at the distal ends of the needles.

In a particularly preferred embodiment, the knotting process is automated as well. To this end, the invention proposes a method of forming a knot in at least one thread, comprising:
applying a tension to a loose end of the thread,
pulling a part of the thread that adjoins the loose end in a direction transverse to the direction of the thread by means of a hook-shaped suction nozzle, and rotating the suction nozzle, thereby to cause the thread to form a loop around the suction nozzle, and
releasing the loose end and then sucking it into the suction nozzle.

In the last step of this method, the loose end of the thread is drawn through the loop, and eventually the loop itself will be drawn into the interior of the suction nozzle, and the knot will be tightened.

In the method according to the invention, the knot will be formed in both of the loose ends of the thread, so that, when the knotted ends are withdrawn from the suction nozzle, the entire thread will securely be fixed at the tampon.

It will of course be understood that the knotting method that has been described above forms an invention by itself and may also be used for other purposes.

The invention further proposes equipment for carrying out the methods that have been described above, as well as a tampon with a thread fixed thereto in accordance with the method according to the invention.

An embodiment of the invention will now be described in conjunction with the drawings, wherein.

Figure 1:
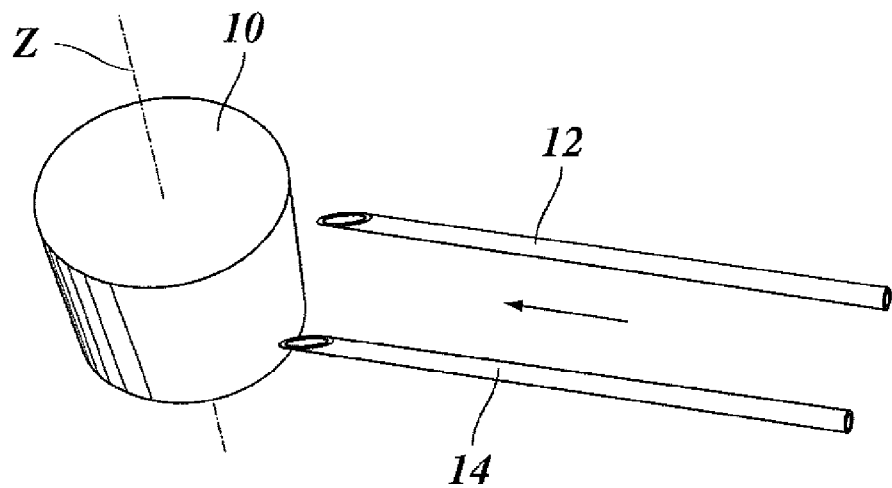
FIG. 1 is a perspective view of a tampon and two needles, illustrating a first step of a method for fastening a thread to the tampon.

As is shown in FIG. 1, a tampon 10 which is formed by a cylindrical piece of sponge is pierced with two hollow needles 12, 14 which extend in parallel with one another and perpendicular to the central axis Z of the cylindrical tampon. The needles 12, 14 are arranged symmetrically with respect to the axis Z and have a mutual spacing that is smaller than the diameter of the tampon. By way of example, the spacing between the two needles 12, 14 amounts about 75% of the tampon diameter.

Figure 2:
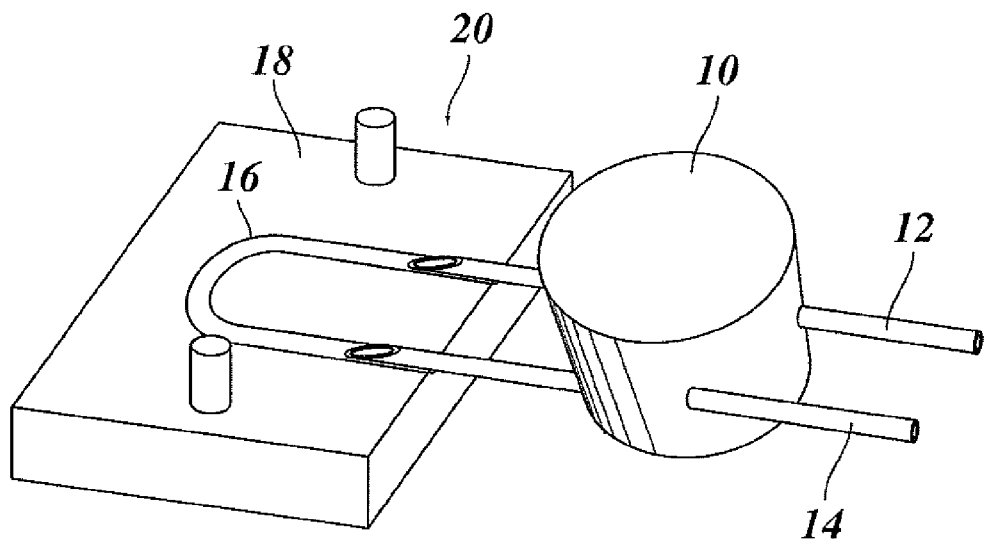
FIGS. 2 to 7 illustrate further steps of the fastening method.

In FIG. 2, the needles 12, 14 have pierced the tampon 10 completely, and their tip ends or distal ends have been inserted into a U-shaped passage 16 formed in a lower half 18 of a mould 20. The passage 16 interconnects the distal ends of the needles 12, 14 and has a half-cylindrical cross-section with a diameter that matches the outer diameter of the needles.

Figure 3:
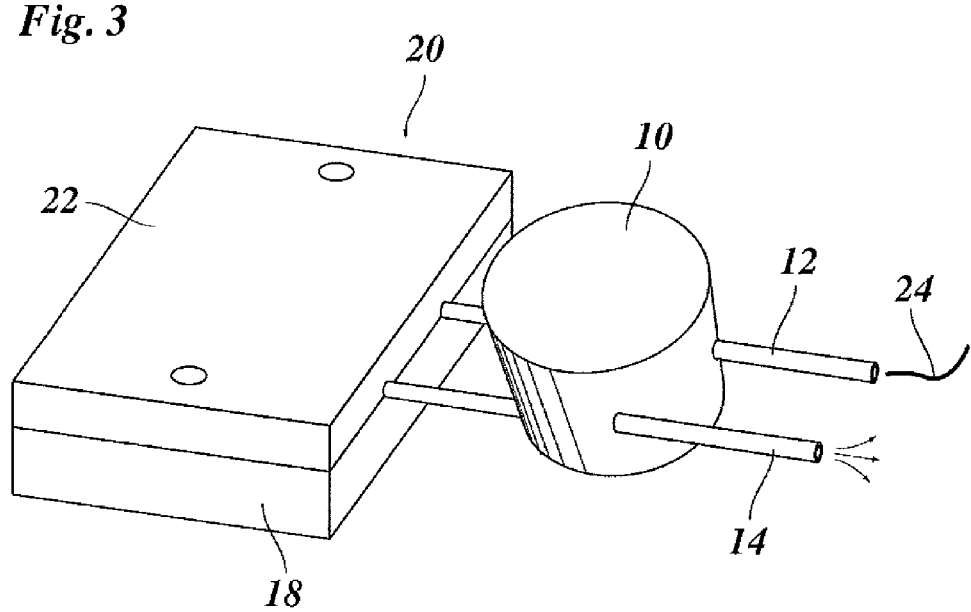

In FIG. 3, the mould 20 has been closed-off by a top half 22 which forms another part of the U-shaped passage 16, complementary to the part shown in FIG. 2. The mould halves 18 and 22 are exactly aligned with one another and are held in close contact with one another, so that the distal ends of the needles 12, 14 are fitted in the open ends of the passage 16 in a substantially air-tight manner. As is further shown in FIG. 3, an end of an endless thread 24 is brought into close proximity of the proximal end of the needle 12. Moreover, a suction pressure is applied to the proximal end of the other needle 14, as has been indicated by arrows in FIG. 3. As a result, the thread 24 is drawn-in into the needle 12 by an air stream passing through the needle 12, the passage 16 and the needle 14.

Figure 4:
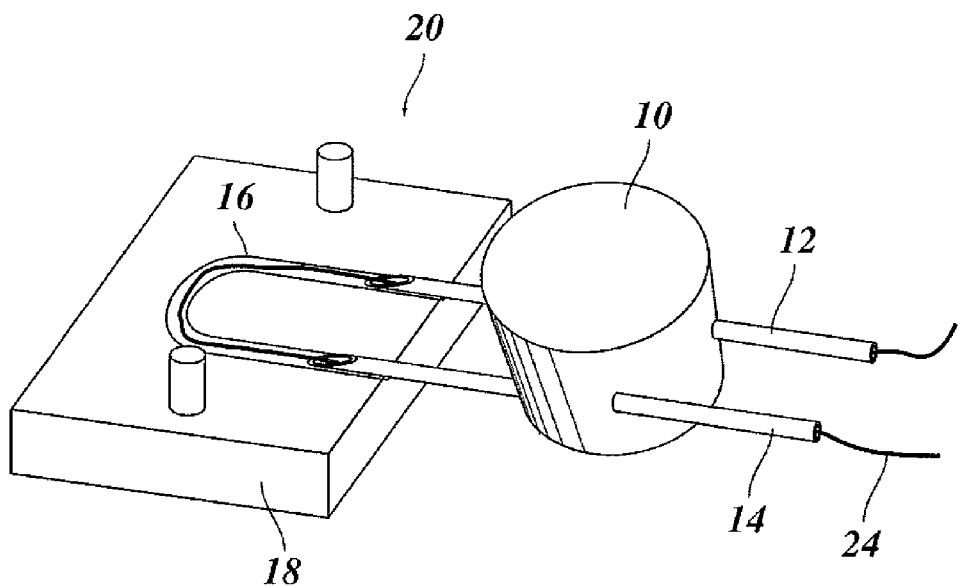

In FIG. 4, the free end of the thread 24 has been blown out of the proximal end of the needle 14. The mould 20 has been opened again, so that a part of the thread 24 is visible in the passage 16. The part of the thread 24 that enters into the proximal end of the needle 12 is cut to a suitable length by means of a cutting tool that has not been shown (it is noted that cutting can also be performed in an earlier or later stage). Then, when the needles 12, 14 are withdrawn from the tampon 10 and the loose ends of the thread 24 (on the side of the proximal ends of the needles) are withdrawn as well, the thread is drawn out of the open mould 20, and a segment 24a of the thread will engage the circumferential surface of the tampon 10, whereas adjoining segments 24b of the thread pass through the interior of the tampon, as has been illustrated in FIG. 5.

Figure 5:
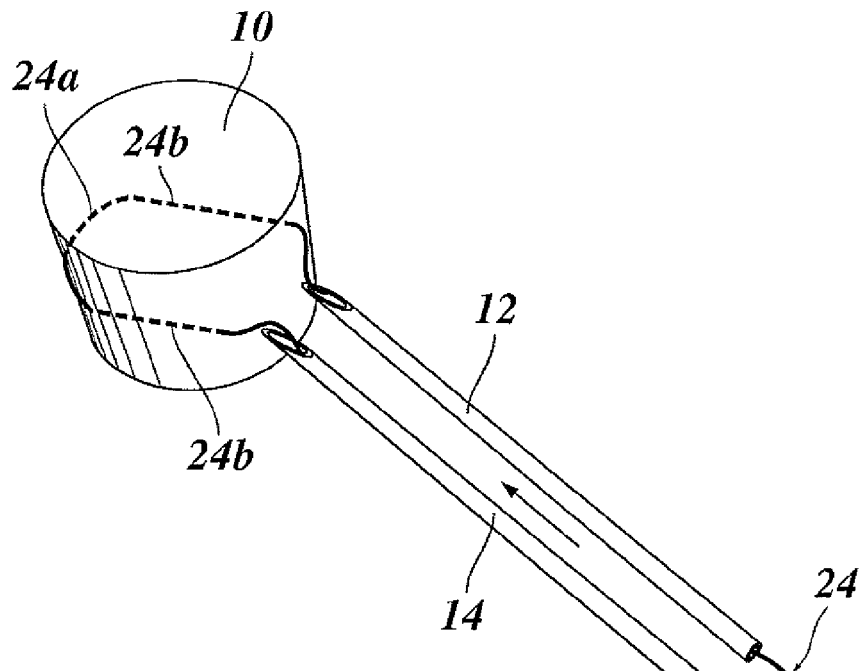

Further, in the condition shown in FIG. 5, the needles 12, 14 have been tilted so as to form an angle of approximately 45° with the central axis of the tampon 10, and the needles have been approached to one another so that their mutual spacing will now amount to only about 40% of the diameter of the tampon, for example. Then, the needles 12, 14 with the thread 24 passing therethrough will again be advanced in longitudinal direction so as to pierce the tampon 10 a second time.

Figure 6:
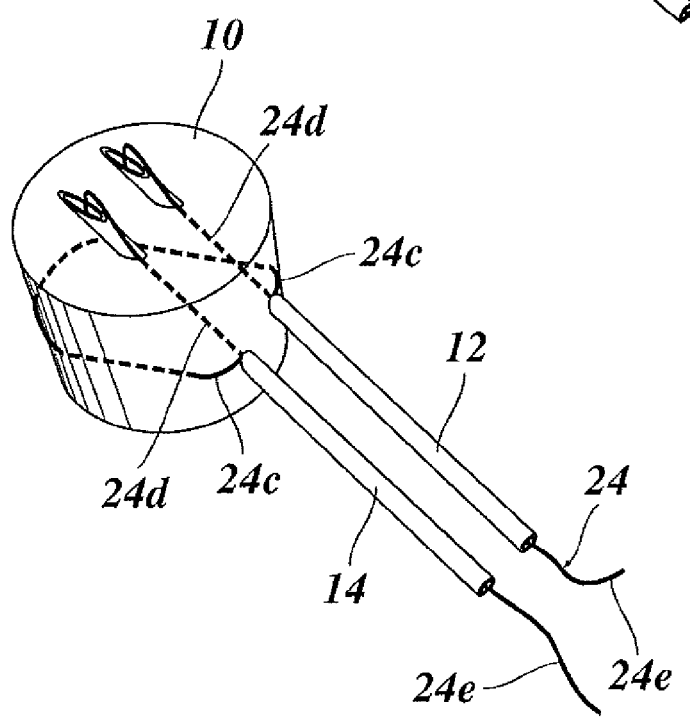

FIG. 6 illustrates the result of this second piercing step and shows that the distal ends of the needles 12, 14 emerge from the top surface of the cylindrical tampon 10 at positions located on a diameter of that top surface and symmetric with respect to the centre thereof. The points where the needles 12, 14 enter through the circumferential surface of the tampon 10 in FIG. 6 are level with the points where the needles have entered in the first piercing step (FIGS. 1 and 2), so that the thread 24 now forms two further segments 24c which extend circumferentially along the peripheral surface of the tampon 10 on the side opposite to the segment 24a. Adjoining segments 24d of the thread have been entrained by the tip ends of the needles 12, 14, so that they now pass through the tampon 10 along the needles 12, 14 but outside of these needles. At the tip ends of the needles, the segments 24d make a sharp turn to form loose ends 24e which pass through the interior of the hollow needles 12, 14 and, in FIG. 6, dangle out of the proximal ends thereof.

Finally, a suction nozzle (not shown here) is brought into the vicinity of the top surface of the tampon 10, and the loose ends 24e of the thread 24 are drawn-out through the distal ends of the needles 12, 14 which are then withdrawn. This leaves the tampon with the tread 24 in the condition shown in FIG. 7.

Figure 8:
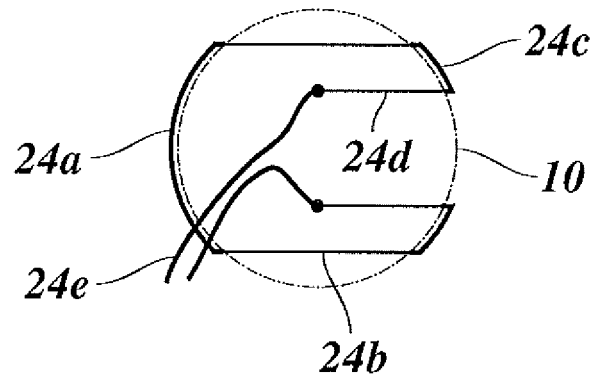
FIG. 8 is a schematic top plan view of the tampon with the thread fastened thereto.
Figure 9:
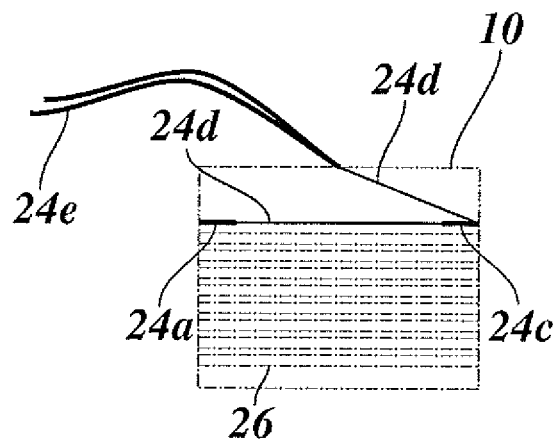
FIG. 9 is a schematic side elevation of the tampon and the thread shown in FIG. 8.

FIGS. 8 and 9 show the various segments 24a-24e of the thread inside and outside of the tampon 10 in a top plan view and a side elevation, respectively. As can be seen in FIG. 9, the thread segments 24a, 24b and 24c lie in a plane that extends in parallel with the top surface of the tampon 10 and is spaced therefrom by a distance that amounts to ¼ of the height of the tampon 10, for example.

When the tampon 10 has been inserted into the vagina of a sheep, for example, and the loose ends 24e of thread 24 (the loose ends have not been shown in their full length in the drawings) are used for pulling the tampon out, the tension of the thread will tend to draw the segments 24a and 24c inwards, so that the sponge material of the tampon will slightly be choked near its proximal end, which facilitates the sliding movement of the tampon in the vagina. Moreover, since the loose ends 24e exit near the centre of the top (proximal) surface of the tampon, they will not cause a substantial torque tending to cant the tampon in the vagina.

Experiments have shown that the arrangement and fastening structure of the thread 24 as described above has a remarkable tensile strength and can withstand a tensile force of about 85 N before the sponge material of the tampon is torn apart, in comparison to only about 65 N for the best known conventional fastening structure.

In spite of the high tensile strength, the fastening structure requires only a relatively short length of the thread 24, so that the consumption of thread material is significantly reduced in comparison to the prior art.

This structure has the further advantage that only relatively small parts of the thread 24, i.e. the segments 24a and 24c, are exposed at the circumferential surface of the tampon and that these segments extend in circumferential direction. This leaves enough space on the peripheral surface of the tampon for impregnating the same with the drug or hormone to be administered. As has been indicated by dot-dashed-lines in FIG. 9, the hormone may be printed onto the peripheral surface of the tampon in the form of endless parallel tracks 26. Since the segments 24a and 24c of the thread extend in the same circumferential direction, they will not interfere with the tracks 26.

In order to safely secure the thread 24, the loose ends 24e may be knotted. A suitable knotting method will now be described in conjunction with FIGS. 10 to 16.

Figure 10:
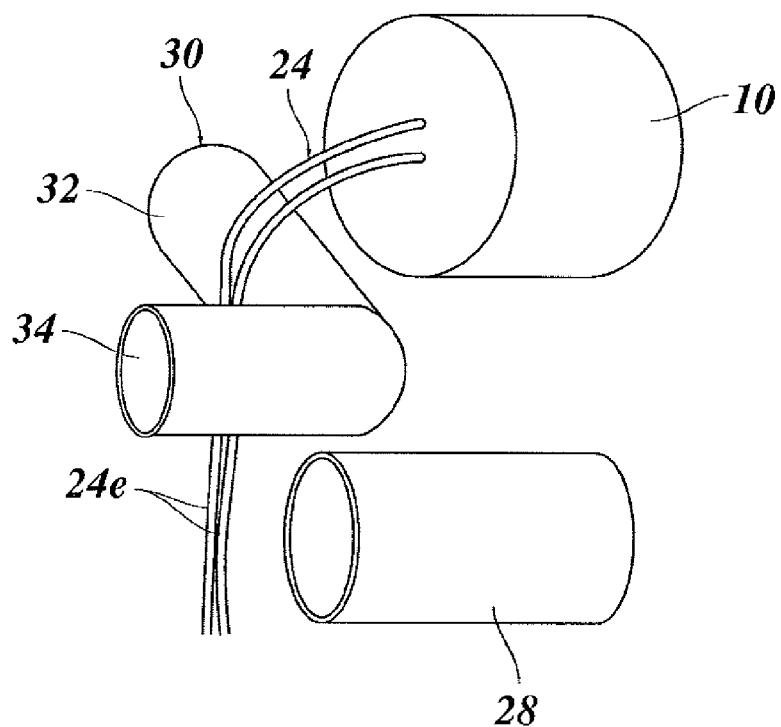
FIGS. 10 to 16 are schematic sketches illustrating the essential steps of a method for forming a knot in the loose ends of the thread.

FIG. 10 shows the tampon 10 with the loose ends 24e of the thread 24 exiting from an end face thereof. A first suction nozzle 28 and a hook-shaped second suction nozzle 30 are disposed in proximity of that end of face of the tampon. The second suction nozzle 30 has a tubular part 32 and a mouth portion 34 forming a right angle with the tubular part. The second suction nozzle 30 is arranged such that the loose ends 24e pass over the peripheral surface of the tubular part 32 and the mouth portion 34 grips around these loose ends as shown in FIG. 10.

Figure 11:
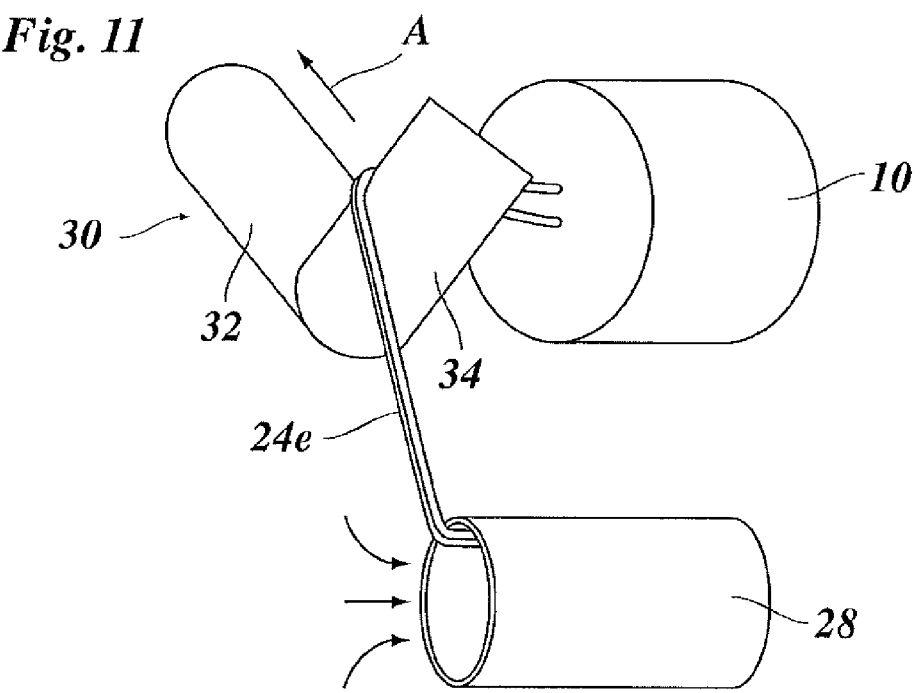

Then, as is shown in FIG. 11, a suction pressure is applied to the first suction nozzle 28, so that air is drawn-in, as has been indicated by arrows in FIG. 11. As a result, the loose ends 24e are drawn into the first suction nozzle 28, and the air stream exerts a certain tensile force on the loose ends 24e. Then, the second suction nozzle 30 is withdrawn in direction of an arrow A, i.e. in axial direction of the tubular part 32, so that the mouth portion 34 deflects the loose ends 24e. Simultaneously or a short time later, the second suction nozzle 30 is caused to rotate (clockwise on FIG. 11) about the longitudinal axis of the tubular part 32.

Figure 12:
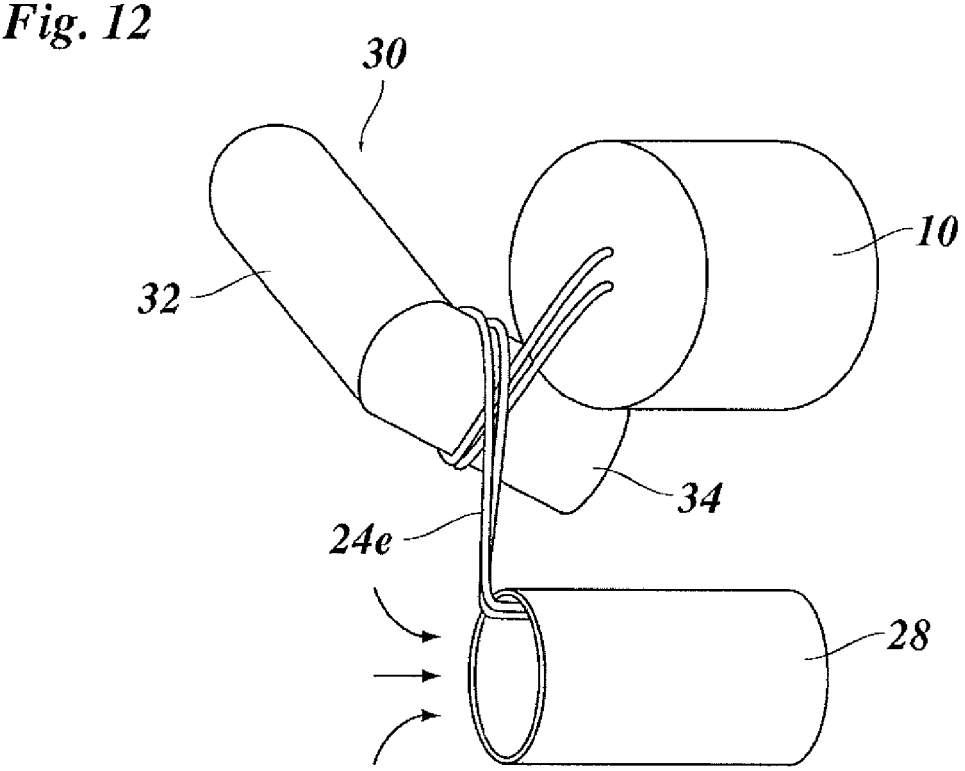
Figure 13:
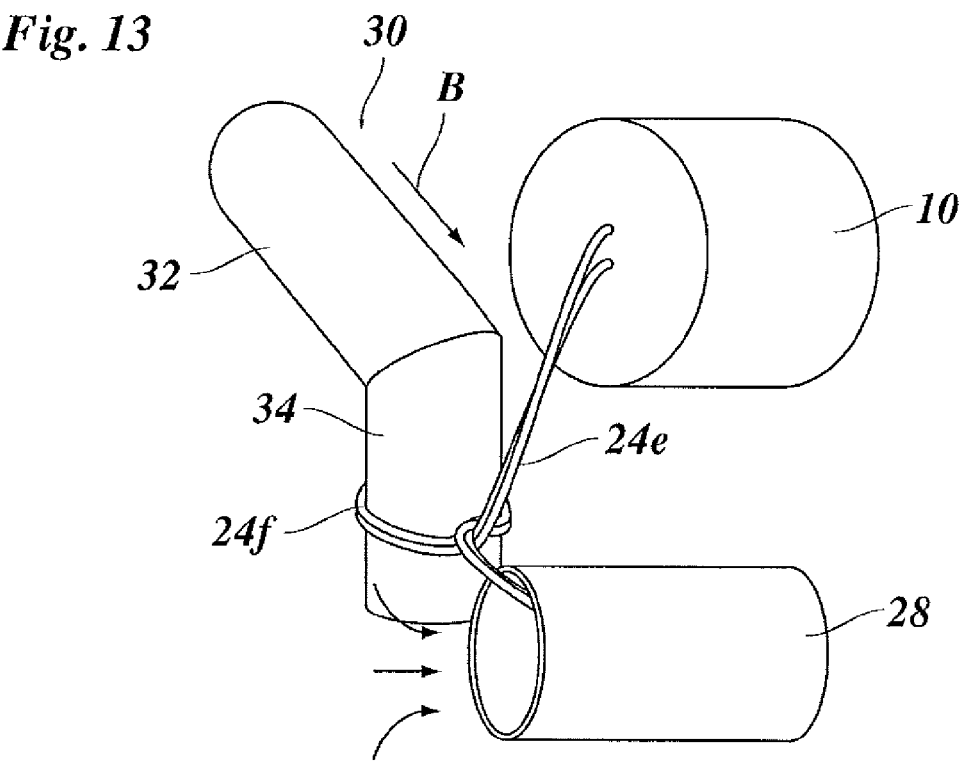

In FIGS. 12 and 13, the axial movement of the second suction nozzle 30 has stopped while the rotation continues and the loose ends 24e are still drawn-in by the first suction nozzle 28 with a certain tensile force. The tilting movement of the mouth portion 34 entrains a part of the loose ends 24e that had been deflected by the withdrawal of the suction nozzle 30. As a result, the loose ends 24e form a loop 24f around the mouth portion 34. In FIG. 13, the second suction nozzle 30 is advanced again in direction of an arrow B, i.e. in axial direction of the tubular part 32.

Figure 14:
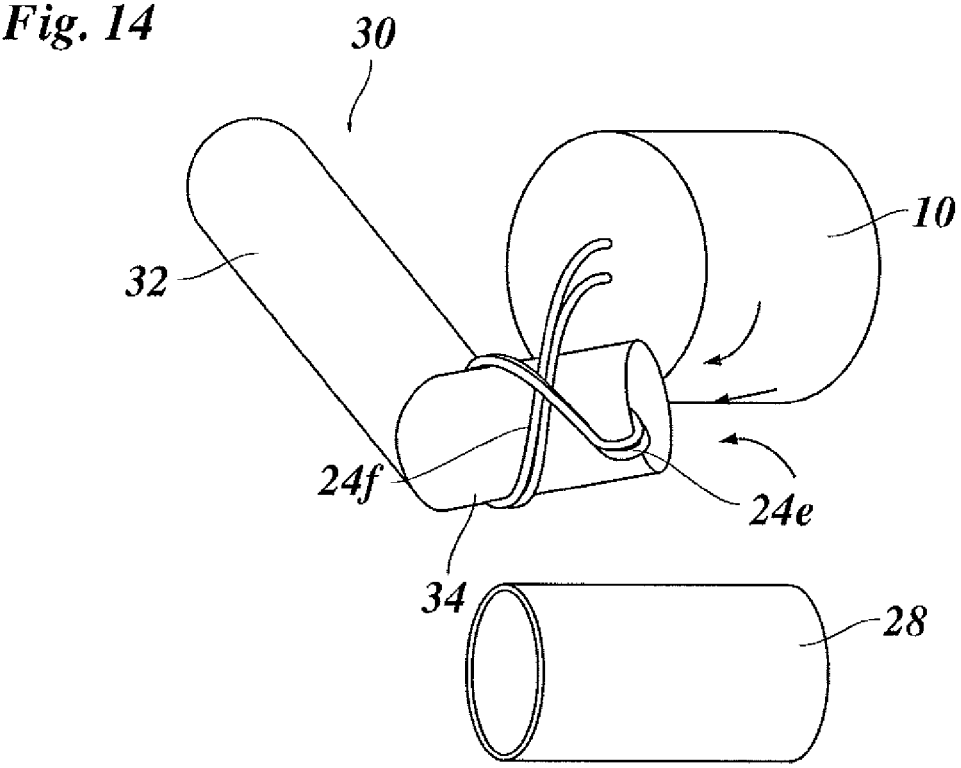

Then, the first suction nozzle 28 is disabled and, instead, a suction pressure is applied to the second suction nozzle 30, so that air is drawn-in through the mouth portion 34 as has been indicated by arrows in FIG. 14. Simultaneously, the second suction nozzle 30 is rotated in counterclock-sense in FIG. 14, so that the mouth portion 34 approaches a position where its open end faces the end face of the tampon 10. While the loop 24f still surrounds the outer periphery of the mouth portion 34, the loose ends 24e of the thread are continuously drawn-in by the second suction nozzle 30, so that the loose ends are caused to pass through the loop 24f inside of the mouth portion 34.

Figure 15:
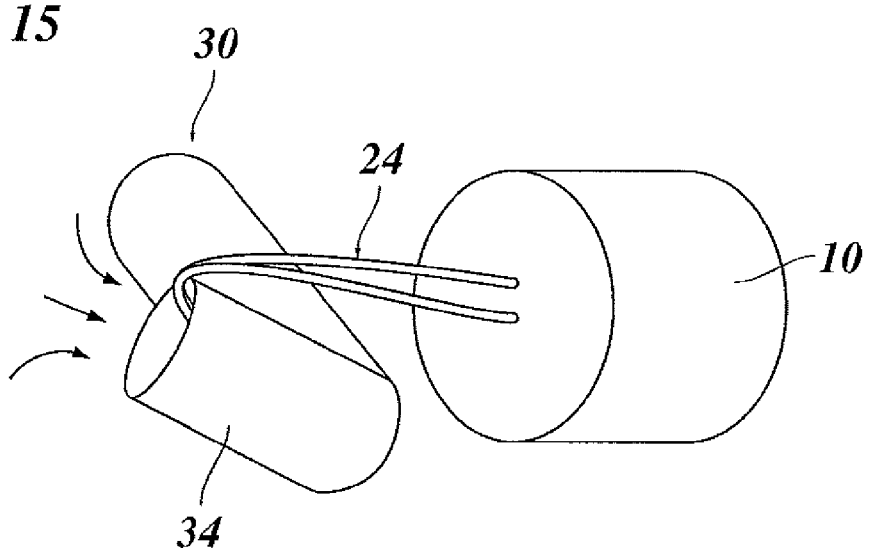

While the suction pressure is still applied to the second suction nozzle and the rotation thereof is continued, the loop 24 slips off from the mouth portion 34 and is also drawn into the interior of the mouth portion, as has been shown in FIG. 15.

Figure 16:
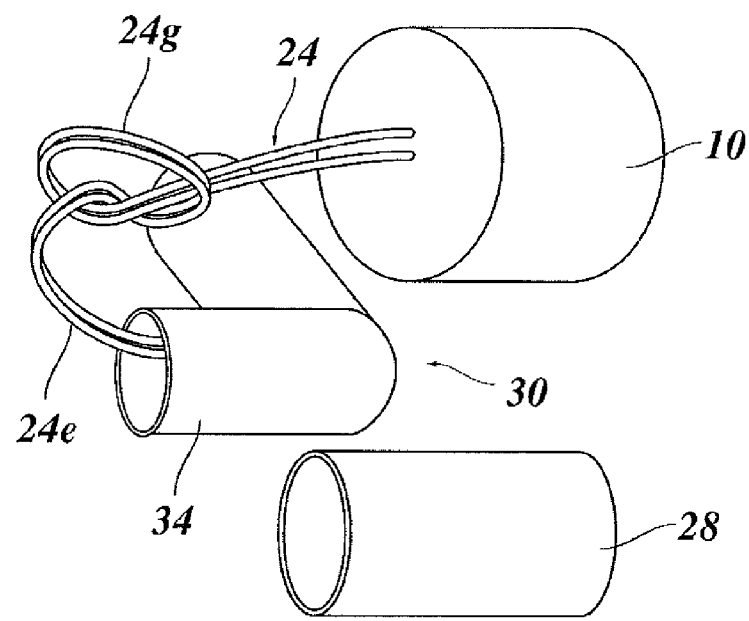

Then, as is shown in FIG. 16, the suction pressure for the second suction nozzle 30 is switched off and this nozzle is returned to the start position that had been shown in FIG. 10. Thus, when the tampon 10 is removed, the loose ends 24e may be drawn out of the mouth portion 34. Since the loose ends have been drawn through the loop 24f (FIG. 14) a knot 24g has been formed. FIG. 16 shows this knot in a relatively loose condition for the sake of clarity. In practice, however, the tensile force applied to the loose ends 24e by the air current inside the suction nozzle 30 will cause the knot 24g to be drawn tight.

Figure 7:
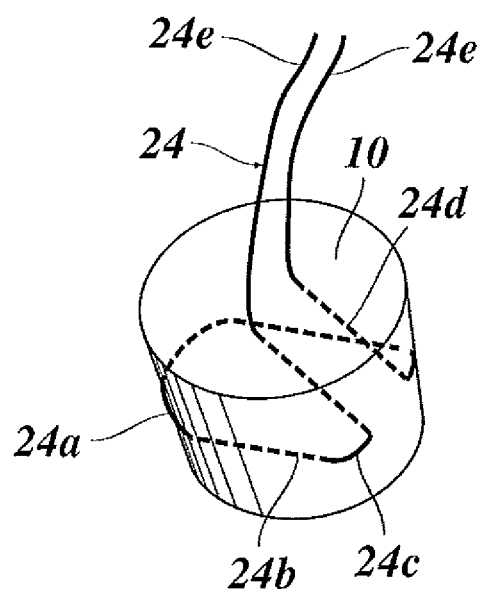

Since the second suction nozzle 30 is arranged in close proximity to the position where the tampon 10 is held, the knot 24g is formed in a short distance from the end face of the tampon 10, which minimises the risk that a pulling force is applied to parts of the thread 24 inside of and around the tampon 10 and destroys the thread configuration shown in FIG. 7.

It should be noted that FIGS. 10 to 16 show the tampon 10 and the suction nozzles 28, 30 from a perspective that is suitable for illustrating the knot forming method. In practise, the tampon and the suction nozzles may be arranged in different relative positions and orientations. For example, the tampon 10 may be held in a position where the end face from which the thread 24 exits faces upward. Then, when the tampon is removed downwardly, the second suction nozzle 30 is preferably held in a position where its mouth portion 34 also faces downward, so that the knotted thread 24 can easily been withdrawn from the suction nozzle.

Figure 17:
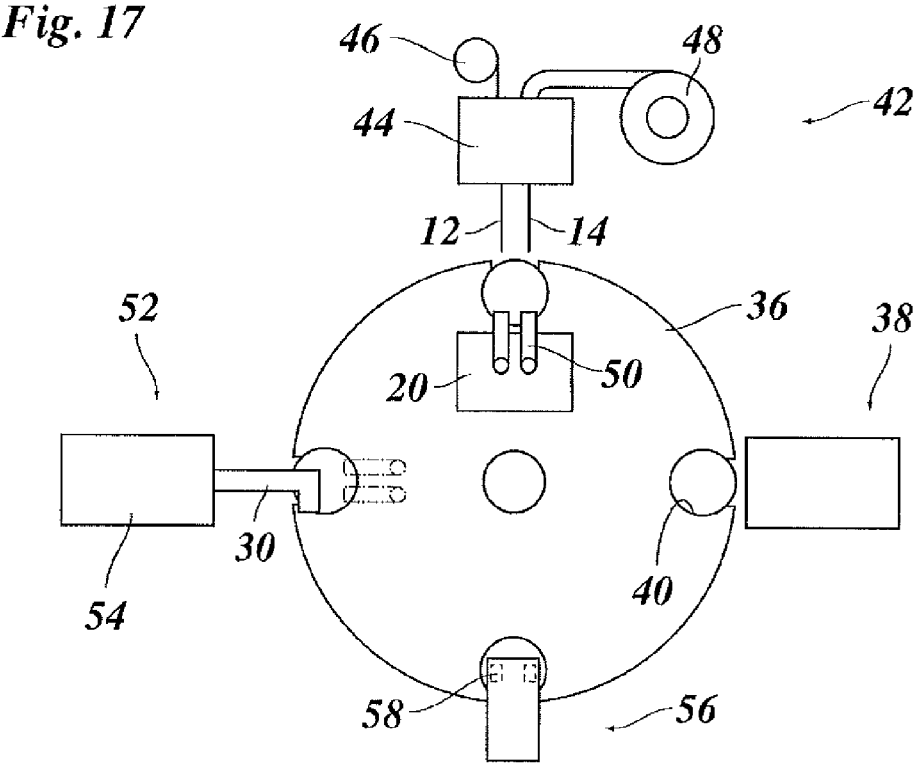
FIG. 17 is a schematic top plan view of an apparatus for performing the method illustrated in FIGS. 1 to 16.

FIG. 17 shows an overall schematic plan view of an apparatus for attaching the thread 24 to the tampon 10. This apparatus comprises a turntable 36 with three to four processing stations disposed at the periphery of the turntable in angular intervals of 90°. A feed station 38 is arranged for inserting a tampon 10 into one of four seats 40 that are formed in the edge portion of the turntable 36 in angular intervals of 90°. The construction of the feed station 38 is straightforward and is not described in detail herein.

When the tampon has been inserted at the feed station 38, the turntable 36 is rotated by 90°, so that the tampon is conveyed to a thread fastening station 42 where the thread is applied to the tampon in accordance with the principles that have been described above in conjunction with FIGS. 1 to 9. In the example shown, the needles 12, 14 are held by a manipulator 44 which controls the piercing movements of the needles (FIGS. 1 and 5) as well as the tilting movements of the needles and the movements for changing the spacing between the needles (FIGS. 4 and 5). A thread feeder 46 has a conventional construction and is arranged for feeding the thread to the proximal end of the needle 12, and a vacuum source 48 is connected to the manipulator 44 for applying a suction pressure to the needle 14 (in another embodiment, the vacuum source applies a positive pressure to needle 12, such that an equivalent pressure difference over the needle ends can be generated. Thus, the term vacuum source covers any source that can impose a pressure difference such that in effect, a suction pressure is generated). The mould 20 and a mechanism (not shown) for opening and closing the mould are disposed on the turntable 36 which also carries a pair of suction nozzles 50 and an associated vacuum source (not shown) for pulling the loose ends of the thread 28 out of the needles 12, 14 in the condition shown in FIG. 6.

Then, the turntable 36 makes another 90° turn for conveying the tampon with the thread fastened thereto to a knotting station 52 which is arranged and functions according to the principles illustrated to FIGS. 10 to 16. The suction nozzles 50 are rotated together with the tampon and keep the loose ends 24e of the thread fixed and may serve as the first suction nozzle 28 (FIGS. 10 to 16) when the knotting station 52 has been reached. The second suction nozzle 30 is mounted on a manipulator 54 which controls the axial and rotary movements of the suction nozzle and also includes a vacuum source for the second suction nozzle so as to perform the operations illustrated in FIGS. 10 to 16. When the knot in the thread has been formed, the turntable 36 conveys the tampon to an ejector station 56 where two plungers 58 are actuated for pressing the tampon 10 downwardly out of the seat 40.

While, in FIG. 17, the ejector station 56 has been shown separately from the knotting station 52 for reasons of clarity of the illustration, it will in practise be preferable to combine the ejector stage with the knotting stage. The plungers 58 will then grip over the mouth portion of the suction nozzle 30 like a yoke to press the tampon downward while the mouth portion of the suction nozzle 30 is also oriented downward for facilitating the withdrawal of the knotted loose ends of the thread.

The invention claimed is:

1. A method for fastening a thread (24) to a tampon (10, comprising the steps of passing the thread through the tampon by means of a needle (12, 14), and knotting the loose ends (24e) of the thread, characterised in that the step of passing the thread through the tampon comprises: piercing the tampon (10) with two hollow needles (12, 14), inserting the distal ends of the needles into a mould (20) that forms a passage (16) interconnecting the open ends of the hollow needles, feeding the thread (24) to the proximal end of one (12) of the two needles, applying a suction pressure to the proximal end of the other (14) of the two needles, opening the mould (20), and—withdrawing the needles (12, 14) from the tampon (10).

2. The method according to claim 1, wherein the tampon (10) has a cylindrical shape and the needles (14), when piercing the tampon (10), are arranged symmetrically with respect to the tampon and in a common plane in parallel to the end faces of the cylindrical tampon.

3. The method according to claim 2, wherein the step of passing the thread (24) through the tampon (10) further comprises: when the needles (12, 14) have been withdrawn from the tampon (10), changing the position and/or orientation of the needles and piercing them through the tampon a second time, —applying a suction pressure to the open tip ends of the needles (12, 14) for forcing the loose ends (24e) of the thread (24) out of the needles.

4. The method according to claim 3, wherein the mutual spacing of the needles (12, 14) is varied before the tampon (100) is pierced the second time.

5. The method according to claim 1, wherein the step of passing the thread (24) through the tampon (10) further comprises: when the needles (12, 14) have been withdrawn from the tampon (10), changing the position and/or orientation of the needles and piercing them through the tampon a second time, —applying a suction pressure to the open ti ends of the needles (12, 14) for forcing the loose ends (24e) of the thread (24) out of the needles.

6. The method according to claim 5, wherein the mutual spacing of the needles (12, 14) is varied before the tampon (1) is pierced the second time.

7. An equipment for carrying out the method according to claim 6 characterised by comprising: a manipulator (44) arranged to hold and move to hollow needles (12, 14), a mould (2) defining a passage (16) interconnecting the open tip ends of the needles (12, 14) when the latter are inserted into two open ends of the passage, a thread feeder (46) arranged to feed a thread (24) to a proximal end of one (12) of the needles, and a vacuum source (48) for applying a suction pressure to a proximal end of the other (14) of the needles.

8. The method according to claim 1, wherein the step of knotting the loose ends (24e) of the thread (24) comprises: applying a tension to the loose ends (24e) of the thread, pulling a part of the thread (24) that adjoins the loose ends (24) in a direction transverse to the direction of the threads by means of a hook-shaped suction nozzle (3), and rotating the suction nozzle, thereby to cause the thread (24) to form a loop (24f) around the suction nozzle, and releasing the loose end (24e) and then sucking it into the suction nozzle (30).

9. The method according to claim 8, wherein the tension is applied to the loose ends (24e) of the thread by means of another suction nozzle (28).

10. An equipment for carrying out the method according to claim 1, characterised by comprising: a manipulator (44) arranged to hold and move to hollow needles (12, 14), a mould (2) defining a passage (16) interconnecting the open tip ends of the needles (12, 14) when the latter are inserted into two open ends of the passage, a thread feeder (46) arranged to feed a thread (24) to a proximal end of one (12) of the needles, and a vacuum source (48) for applying a suction pressure to a proximal end of the other (14) of the needles.

11. The equipment according to claim 10, wherein a thread fastening station (42) comprising the manipulator (44), the thread feeder (46) and the vacuum source (48) is disposed at a conveyer (36) that is arranged to convey a tampon (10) into and out of a position where it can be pierced with the needles (12, 14).

12. The equipment according to claim 11, including a knotting station (52) that comprises a first suction nozzle (28, 50) adapted to hold loose ends (24e) of the thread, a hook-shaped second suction nozzle (3), and a manipulator (54) arranged to rotate and axially displace the second suction nozzle (3) relative to the first suction nozzle (28).

13. The equipment according to claim 12 wherein the conveyer is configured as a turntable (36), and the first suction nozzle (50) is arranged to co-rotate with the turntable (36).

14. The equipment according to the claim 10, including a knotting station (52) that comprises a first suction nozzle (28, 50) adapted to hold loose ends (24e) of the thread, a hook-shaped second suction nozzle (3), and a manipulator (54) arranged to rotate and axially displace the second suction nozzle (3) relative to the first suction nozzle (28).

15. The equipment according to claim 14, wherein the conveyer is configured as a turntable (36), and the first suction nozzle (5) is arranged to co-rotate with the turntable (36).

* * * * *